United States Patent [19]
Brinkmann et al.

[11] 3,941,753
[45] Mar. 2, 1976

[54] PREPOLYMERS OF POLYISOCYANATES WITH HYDROXY-ENAMINES OR HYDROXY-KETIMINES

[75] Inventors: Bernd Brinkmann, Bad Zwischenahn; Eugen Griebsch, Unna, both of Germany

[73] Assignee: Schering Aktiengesellschaft, Berlin and Bergkamen, Germany

[22] Filed: Nov. 1, 1974

[21] Appl. No.: 520,356

Related U.S. Application Data

[63] Continuation-in-part of Ser. No. 240,762, April 3, 1972, Pat. No. 3,865,791.

[30] Foreign Application Priority Data

Nov. 10, 1973  Germany............................ 2356213
Apr. 6, 1971  Germany............................ 2116882

[52] U.S. Cl. .................... 260/77.5 MA; 260/75 NT; 260/77.5 AQ; 260/77.5 AN
[51] Int. Cl.².......................................... C08G 18/02
[58] Field of Search 260/77.5 AQ, 77.5 MA, 75 NT, 260/77.5 AN

[56] References Cited
UNITED STATES PATENTS

| 3,043,801 | 7/1962 | Wagner et al................ 260/77.5 AQ |
| 3,388,100 | 6/1968 | Thoma et al................ 260/77.5 AQ |

FOREIGN PATENTS OR APPLICATIONS

| 1,064,841 | 4/1967 | United Kingdom......... 260/77.5 AQ |

*Primary Examiner*—Ronald W. Griffin
*Attorney, Agent, or Firm*—Curtis, Morris & Safford

[57] ABSTRACT

Prepolymers having enamine or ketimine groups therein are prepared by reacting a polyisocyanate with a mono-enamine or mono-ketimine having an hydroxy group. The prepolymers may be used as mixtures with further isocyanate, which mixtures harden in the presence of water or atmospheric moisture and are useful as lacquers, casting and patching resins, and for coatings and laminates.

3 Claims, No Drawings

PREPOLYMERS OF POLYISOCYANATES WITH HYDROXY-ENAMINES OR HYDROXY-KETIMINES

This application is a continuation-in-part of copending, commonly-owned, allowed U.S. Pat. application Ser. No. 240,762 filed Apr. 3, 1972, now U.S. Pat. No. 3,865,791, issued Feb. 11, 1975.

The aforementioned pending U.S. patent application, incorporated herein by reference, teaches the preparation of stable mixtures which form polyurea polymers in the presence of water. The mixtures comprise at least one polyisocyanate and, inter alia, a prepolymeric reaction product of a polyisocyanate and an enamine having at least one hydroxy group.

The present application relates to prepolymers containing an enamine or ketimine group.

As disclosed in the aforementioned copending application, compounds having an enamine group and an hydroxy group are prepared by reacting a compound having at least one secondary amino group and at least one aliphatic hydroxy group per molecule, e.g. N-(hydroxy-lower alkyl) piperazines such as N-(2-hydroxyethyl)-piperazine or N-(2-hydroxypropyl)-piperazine with (a) an aliphatic aldehyde of the formula

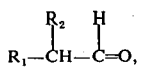

wherein $R_1$ and $R_2$, which may be the same or different, are hydrogen, methyl, or ethyl (e.g. isobutyraldehyde), or with (b) a cycloaliphatic ketone of the formula

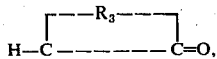

wherein $R_3$ is a trimethylene or tetramethylene group optionally substituted with one or more alkyl groups and having altogether up to 8 carbon atoms.

The reaction may proceed with the addition of heat, with cooling, or at room temperature, and may take place in or without an inert solvent. The reagents are reacted in stoichiometric amounts or, preferably, with the cheaper carbonyl reactant in stoichiometric excess. The water of reaction and any excess carbonyl compound are removed.

Water can be removed using dehydrating agents such as calcium oxide, sodium sulfate, or the so-called "molecular sieves". Most conveniently it is removed by azeotropic distillation using an organic solvent, or the excess carbonyl compound, as the entraining agent.

Acids may optionally be used in small quantity to catalyze the reaction. Although mineral acids may be employed, organic acids such as formic, acetic, or p-toluene sulfonic acids are preferred. Acid anion exchange resins can also be used as catalysts.

Typically, a secondary diamine is combined with an excess of the carbonyl component for reaction and, after the addition of a suitable solvent such as toluene or benzene, the mixture is heated in a water separator under an inert atmosphere, such as of nitrogen, until water separation is complete. In certain cases, the carbonyl compound itself can serve as an entraining agent. Thus, secondary amines can be reacted with a reactive aldehyde such as isobutyraldehyde, using the latter as an entraining agent, at temperatures from about 70° – 100°C. (The boiling point of isobutyraldehyde is about 64°C.) With less reactive reagents, such as the ketones, higher-boiling entraining agents such as benzene, toluene, xylene, or other solvents inert to amines and forming azeotropes with water, can be employed.

Distillation of the product is not strictly necessary. The crude product can be directly employed after removal of excess carbonyl component and solvent.

Aliphatic aldehydes and cyclic ketones are particularly suitable as the carbonyl component. Examples of aldehydes and ketones which can be used to advantage in the preparation of polyenamines according to the invention are: acetaldehyde, propionaldehyde, n-butyraldehyde, isobutyraldehyde, diethyl acetaldehyde, cyclopentanone, trimethyl cyclopentanone, cyclohexanone, trimethyl cyclohexanone, and other substituted cyclohexanones and cyclopentanones.

The less reactive aliphatic ketones give less good yields.

Compounds containing an hydroxy group and a ketimine group are prepared by reacting a compound having at least one primary amino group and at least one aliphatic hydroxy group per molecule with an aliphatic ketone of the formula

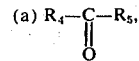

wherein $R_4$ and $R_5$, which may be the same or different are lower alkyl, or (b) a cycloaliphatic ketone of the formula

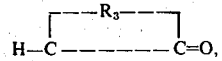

wherein $R_3$ has its earlier meaning.

Suitable primary hydroxy amines are hydroxyalkyl primary amines having 2 to 6 carbon atoms, such as ethanolamine and hexanolamine-1,6, and hydroxy lower alkyl lower alkoxy primary amines such as diglycolamine.

Examples of ketones which can be used to advantage for the preparation of ketimines are: cyclopentanone, trimethylcyclopentanone, cyclohexanone, trimethylcyclohexanone, other substituted cyclohexanones and cyclopentanones, methylisobutylketone, methylethylketone, diethylketone, diisopropylketone, and the like.

The ketimines are prepared under the same conditions as the enamines.

For formation of prepolymers, the hydroxy-enamines or hydroxy-ketimines are reacted by mixing them with an amount of polyisocyanate, preferably an aliphatic polyisocyanate, such that the ratio NCO/OH is 1. Mixing should be effected with vigorous stirring until no free isocyanate can be detected, e.g. by infrared spectroscopy. Optionally, the mixtures may be cooled to temperatures from 0°–30°C. during the reaction.

It has heretofore not been known that ketimines containing hydroxy groups could be added to isocyanates, with the formation of urethane groups, with retention of the ketimine structure in its original form. Rather, it has been described in the literature that ketimines react with isocyanates with the formation of cyclic addition products or products containing amide groups or urea groups [K. Harada, Makromol. Chem.

132, 295–304 (1970)].

As examples of organic polyisocyanates which can be reacted with hydroxy-enamines or hydroxy-ketimines according to the invention are: aromatic polyisocyanates such as 2,4- and 2,6-toluene diisocyanate, 4,4'-diisocyanato-diphenylmethane, or 1,5-naphthalene diisocyanate; aliphatic diisocyanates, such as hexamethylene diisocyanate, trimethylhexamethylene diisocyanate, dimeryl-diisocyanate (dimeryl = the radical of a dimerized fatty acid); cycloaliphatic diisocyanates such as dicyclohexyl-methane diisocyanate or isophorone-diisocyanate (i.e. 1-isocyanato-3-isocyanatomethyl-3,5,5-trimethylcyclohexane); triisocyanates containing biuret groups; the reaction products of polyols, for example low molecular weight aliphatic polyols or polybutadiene diols, with polyisocyanates; and prepolymeric isocyanates which are prepared by reaction of an excess of diisocyanate with polyesters or polyethers containing free hydroxy-groups.

Particularly preferred prepolymers are obtained by reacting the hydroxy-enamine or hydroxy-ketimine with a polyisocyanate pre-adduct prepared from a polypropylene glycol and an excess (NCO/OH = 1.8 to 2.2) of an aliphatic diisocyanate.

The polypropylene glycols are suitably linear or branched products having an average molecular weight between about 500 and about 10,000.

For pre-adduct formation, it is advantageous to employ aliphatic diisocyanates having isocyanate groups of differing reactivity, since in this manner a chain lengthening is avoided. Such diisocyanate is, for example, isophorone diisocyanate. In those cases in which a chain lengthening is desired, hexamethylene diisocyanate, 1-methyl-2,4-diisocyanatocyclohexane, or 4,4'-diisocyanatodicyclohexylmethane can be used.

In general, it is suitable to mix the components, with cooling, at 0°–30°C. and to add a catalyst such as, for example, organic tin compounds or tertiary amines. Subsequently, the mixture is warmed to an elevated temperature, preferably from 50°–100°C., until the analytically-determined isocyanate content corresponds with the calculated value.

The pre-adducts and an hydroxy-enamine or hydroxy-ketimine are then reacted in an equivalent amount as heretofore described to form the desired prepolymers.

For formation of a storage-stable mixture hardenable in the presence of water one or more of the enamine or ketimine prepolymers described above is admixed with an equivalent amount of at least one organic polyisocyanate, which may be "capped". As capped polyisocyanates useful for this purpose, adducts of trimethylolpropane and 2,4-toluolylene-diisocyanate in a mol ratio of 1:3 are employed, for example, wherein the free isocyanate groups can be capped with phenol. Further, adducts of polypropylene glycols and 2,4-toluoylene-diisocyanate having residual isocyanate groups capped with nonphenol can be employed.

In the presence of water, these mixtures form polyurea compounds, suitably while the reaction mass is being shaped. Thus, the mixtures are particularly useful for the preparation of lacquers, casting and patching resins, and for forming coatings and laminates. For application, the mixtures are a. combined with water and applied in the desired manner or b. applied in the desired way and then subjected to the influence of water, steam, or atmospheric moisture. Amounts of water less than are equivalent to the enamine or ketimine content are suitable for effecting hardening.

A better understanding of the present invention and of its many advantages will be had by referring to the following examples, given by way of illustration.

EXAMPLE 1 a. 50 parts of N-(2-hydroxyethyl)-piperazine are heated for 15 hours in a water separator with 27.7 parts of isobutyraldehyde and 30 parts of toluene. Thereafter, excess aldehyde and toluene are removed and the residue is distilled in vacuum.

B.p. = 112°C./2.5 mm Hg

| Analysis (Percent by Weight) | Calculated for Enamine | Found |
|---|---|---|
| C | 65.3 | 63.7 |
| H | 10.8 | 11.1 |
| N | 15.2 | 15.6 | b. 20 parts of a triisocyanate prepared from a branched polypropylene glycol and from isophorone diisocyanate (1-isocyanato-3-isocyanatomethyl-3,5,5-trimethyl-cyclohexane) are reacted with 1.84 parts of the enamine of 1(a) containing an hydroxy group by heating for one hour at 80°C.

EXAMPLE 2 a. A mixture of 60 parts of N-(2-hydroxyethyl)-piperazine, 45 parts of cyclohexanone, and 45 parts of toluene is combined with a catalytic amount of formic acid and heated in a water separator until the reaction is concluded (about 30 hours). After removal of the toluene, the residue is distilled and an enamine of the formula

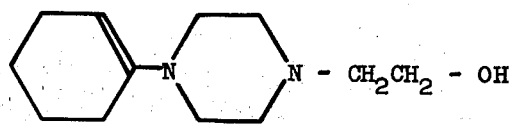

is obtained.

B.p. = 120°C./0.01 mm Hg.

b. 100 parts by weight of a branched polyether having a molecular weight of 4700, obtained by the reaction of trimethylolpropane with propylene oxide, are reacted with 11.1 parts of 2,4-toluene diisocyanate at 70°C. A reaction product having an isocyanate content of 2.5 percent is obtained.

50 parts of this product are stirred for 10 hours at 25°–30°C. with (a) 6.05 parts of 1-(2-hydroxyethyl)-4-cyclohexenyl-piperazine (cf. Example 2a). A further 50 parts of the product were heated for 2.5 hours at 70°C. with (b) 6.8 parts of nonyl phenol and 0.1 percent of dibutyl tin dilaurate. A blend of (a) and (b) produces a product which is storage-stable over several month. However, when exposed to atmospheric moisture a sample of the product hardens in several days to form an elastic transparent product.

| Analysis (Percent by Weight) | Calculated for Enamine | Found |
|---|---|---|
| C | 68.6 | 67.9 |

| Analysis (Percent by Weight) | Calculated for Enamine | Found |
|---|---|---|
| H | 10.5 | 10.7 |
| N | 13.3 | 13.8 |

EXAMPLE 3 a. 91.5 g of ethanolamine, 225 g of methylisobutylketone, and 100 ml of benzene are put into a 1-liter, three-necked flask with a water separator and stirrer.

The mixture is heated under reflux until the calculated water of reaction has been separated.

Then, excess ketone and solvent are removed and the residue is distilled in vacuum. B.p. 53°C./0.5 mm Hg

| Analysis | C | H | N |
|---|---|---|---|
| Calculated | 67% | 11.9% | 9.8% |
| Found | 66.8% | 12.1% | 9.8% |

In the infrared spectrum, there is a strong ketimine band at 1655 cm$^{-1}$.

The formula of the reaction product is

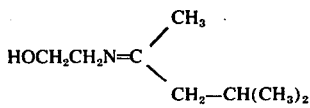

b. A mixture of 5040 g of a trifunctional polypropylene glycol having an OH number of 35.6 and 711 g of isophorone diisocyanate is combined with 5.7 g of dibutyltin dilaurate and stirred for 3 hours under nitrogen at 75°C. The reaction product has an isocyanate content of 2.2 percent by weight, corresponding with an equivalent weight of 1914.

c. 100 g of the pre-adduct containing isocyanate groups prepared according to part (b) above are reacted, with cooling, with 74.83 g of the ketimine containing hydroxyl groups prepared according to (a) above. The materials are vigorously stirred making sure that the temperature does not rise above 30°C.

After 4 to 5 hours of stirring, no more free isocyanate can be detected in the infrared spectrum. In contrast, the ketimine band remains. The product has an equivalent weight of 2057.

EXAMPLE 4 a. A mixture of 105 g of diglycolamine and 150 g of cyclohexanone is combined with 100 ml of benzene and heated for 4 hours with separation of water. 17.6 g of water separate.

The excess ketone and the solvent are removed and the residue is distilled in vacuum. B.p. 103°C./0.2 mm Hg

| Analysis | C | H | N |
|---|---|---|---|
| Calculated | 64.8% | 10.3% | 7.6% |
| Found | 64.8% | 10.3% | 8.0% |

The reaction product has the formula

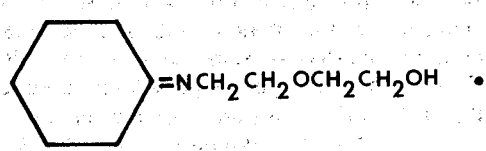

b. 1000 g of the pre-adduct containing isocyanate groups prepared according to Example 3(b) above are mixed with 96.6 g of the ketimine prepared according to Example 4(a) above with cooling and vigorous stirring.

The temperature is kept below 30°C. during the reaction. After 5 hours of stirring, no free isocyanate can be detected in the infrared spectrum. The product has an equivalent weight of 2100.

EXAMPLE 5 a. 324 g of diglycolamine are combined with 300.5 g of methylisobutylketone and 300 ml of benzene.

The mixture is heated in a water separator under nitrogen until water separation is concluded. The solvent is removed and the residue is distilled in vacuum. The reaction product has the formula

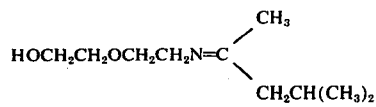

b. 1000 g of the pre-adduct containing isocyanate groups prepared according to Example 3(b) are combined with 97.8 g of the ketimine prepared according to Example 5(a).

After four hours' stirring, no free isocyanate is detected by infrared spectroscopy. The product has an equivalent weight of 2012.

EXAMPLE 6 a. 117 g of hexanolamine-1,6 are heated in a water separator with 150 g of cyclohexanone and 100 ml of benzene until no further water of reaction is formed. The reaction is completed after about 6 hours.

The excess ketone and benzene are removed under vacuum and the residue is distilled in vacuum. B.p. 153°C./0.8 mm Hg

| Analysis | C | H | N |
|---|---|---|---|
| Calculated | 73.0% | 11.7% | 7.1% |
| Found | 73.5% | 11.7% | 6.8% |

The infrared spectrum shows a strong C=N-band at 1660 cm$^{-1}$. The reaction product has the formula

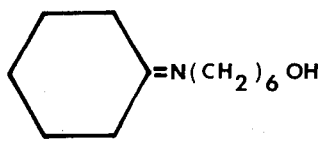

b. 1536 g of a branched polypropylene glycol having an OH-number of 35.6 are combined with 221 g of isophorone diisocyanate and 1.8 g of dibutyltin dilaurate.

The reaction mixture is warmed to 75°C. and held at this temperature for 2.5 hours with good stirring. The reaction product has an isocyanate content of 2.39%.

c. 1000 g of the isocyanate pre-adduct prepared according to part (b) above are stirred at room temperature with 112.2 g of the ketimine containing hydroxy groups prepared according to part (a) of this Example. After the mixture has stood for about 12 hours, no free isocyanate is detectable by infrared spectroscopy.

What is claimed is:

1. A prepolymer, free of isocyanate groups and containing an enamine or ketimine group, prepared by reacting a polyisocyanate and an enamine or ketimine having at least one hydroxy group in an amount such that the ratio NCO/OH is 1.

2. A prepolymer as in claim 1 wherein said polyisocyanate is an aliphatic polyisocyanate.

3. A prepolymer as in claim 1 wherein said polyisocyanate is a pre-adduct prepared by the reaction of a polypropylene glycol with excess diisocyanate.

* * * * *